United States Patent [19]

Zurenko et al.

[11] Patent Number: 4,895,870
[45] Date of Patent: Jan. 23, 1990

[54] TREATING CHLAMYDIA INFECTIONS USING SPECTINOMYCIN ANALOGS

[75] Inventors: Gary E. Zurenko, Alamo Township, Kalamazoo County; James J. Vavra, Portage; David R. White, Kalamazoo; Richard C. Thomas, Oshtemo Township, Kalamazoo County, all of Mich.

[73] Assignee: The Upjohn Company, Kalamazoo, Mich.

[21] Appl. No.: 933,641

[22] PCT Filed: Mar. 26, 1986

[86] PCT No.: PCT/US86/00620
§ 371 Date: Nov. 10, 1986
§ 102(e) Date: Nov. 10, 1986

[87] PCT Pub. No.: WO86/05686
PCT Pub. Date: Oct. 9, 1986

[51] Int. Cl.$^4$ .......................................... A61K 31/335
[52] U.S. Cl. ..................................................... 514/452
[58] Field of Search ......................................... 514/452

[56] References Cited

U.S. PATENT DOCUMENTS

| | | | |
|---|---|---|---|
| 3,234,092 | 2/1966 | Bergy et al. | 167/65 |
| 4,173,647 | 11/1979 | Maier et al. | 424/283 |
| 4,351,771 | 9/1982 | White et al. | 549/361 |
| 4,361,701 | 11/1982 | White | 549/361 |
| 4,465,848 | 8/1984 | Thomas et al. | 549/361 |
| 4,532,336 | 7/1985 | White | 549/361 |

OTHER PUBLICATIONS

Manual of Antibiotics and Infectious Diseases, John E. Conte, Jr., and S. L. Barriere, pp. 292–93, (1984).
Medical Microbiology and Infections Diseases, A. I. Braude, pp. 516–22, (1981).
Zinsser Microbiology, by W. K. Joklik, et al., 18th ed., pp. 785–92, (1984).
Annals of Internal Medicine, vol. 84, "Spectinomycin", W. M. McCormack and M. Finland, pp. 712–16, (1976).
Infectious Diseases, 3rd ed., "Nongonococcal Urethritis," W. R. Bowie and K. K. Holmes, pp. 574–79, (1983).
Antibiotics and Chemotherapy, vol. XI, No. 2, "Actinospectacin, A New Antibiotic III . . . ," Charles Lewis and Howard W. Clapp, pp. 127–33, (1961).
Antimicrobial Agents and Chemotherapy, vol. 2, No. 6, "In Vitro Antibacterial Activity of Spectinomycin," John A. Washington II and Pauline K. W. Yu, pp. 427–30, (1972).
The Journal of Infectious Diseases, vol. 130, No. 1, "Animal and Human Tolerance of High—Dose Intramuscular Therapy with Spectinomycin," Ervin Novak et al., pp. 50–55, (1974).
International Journ. Clin. Pharmacol., 14, "Absorption Distribution and Elimination of Spectinomycin Dihydrochloride in Man," J. G. Wagner et al., pp. 261–85, (1967).
Brit. J. vener, Dis., 46, "Spectinomycin in the Treatment of Uncomplicated Gonorrhoea," Charles E. Cornelius III and Gerald Domescik, pp. 212–13, (1970).
Physicians Desk Reference, 35th ed., Medical Economics Co., p. 1844, (1981).
The Journal of Antibiotics, 26, No. 3, "Synthesis and In Vitro Antibacterial Properties . . . ," D. R. White et al., pp. 339–42, (1983).
The American Journal of the Medical Sciences, 244, "An Evaluation of a New Antibiotic, Actinospectacin . . . ," Robert I. Lindemeyer et al., pp. 480–83, (1962).

Primary Examiner—Jerome D. Godlberg
Attorney, Agent, or Firm—Paul J. Koivuniemi

[57] ABSTRACT

Spectinomycin analogs of formula I, wherein R is alkyl, are used in the treatment of gonococcal, non-gonococcal and post-gonococcal urethritis and chlamydia infections.

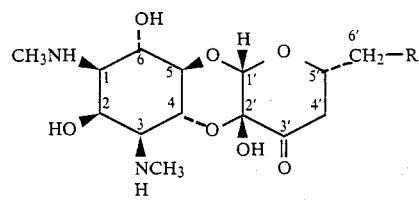

12 Claims, No Drawings

TREATING CHLAMYDIA INFECTIONS USING SPECTINOMYCIN ANALOGS

Chlamydia infect many vertebrate hosts including birds, mammals, and humans. Human diseases caused by *Chlamydia trachomatis* include trachoma, urethritis, inclusion conjunctivitis, lymphogranuloma venereum, cervicitis, salpingitis, infant pneumonitis syndrome and pelvic inflammatory disease.

*C. trachomatis* infections of the genital tract represent the major focus of recent clinical interest in chlamydia. *C. trachomatis* is now recognized as one of the chief causes of both non-gonococcal and post-gonococcal urethritis and cervicitis. In addition, infants born to mothers infected with *C. trachomatis* can also become infected and develop inclusion conjunctivitis, pneumonia, or otitis media. Studies have shown that 60–70% of exposed infants will develop some tupe of *C. trachomatis* infection.

*C. trachomatis* infections are amenable to chemotherapy, with the drugs of choice being tetracycline and erythromycin. However, the use of tetracycline is contraindicated for pregnant women and small children (two large target populations) and a significant number of patients (especially pregnant women) experience gastrointestinal distress from erythromycin and stop taking the drug. A clinical need, therefore, exists for a non-toxic antibiotic that inhibits *C. trachomatis*, *Neisseria gonorrhoeae* and Ureaplasma in combination, or *C. trachomatis* alone.

Evidence now indicates that Ureaplasma causes 7–10% of nongonococcal urethritis. Spectinomycin is useful for treating gonorrhea and nongonococcal urethritis (NGU) caused by *Ureaplasma urealyticum*. On the other hand, it has been shown to have only slight activity against *C. trachomatis* [W. M. McCormack and M. Finland, "Spectinomycin," *Ann. Intern. Med.*, 84, pp. 712–16 (1976)]. Treatment with spectinomycin produces a significantly better response in chlamydia-negative, ureaplasma-positive NGU than in chlamydia-positive, ureaplasma-negative NGU [W. R. Bowie and K. K. Holmes, "Nongonococcal Urethritis", in *Infectious Diseases*, P. D. Hoeprich, ed., pp. 574–79 (1983)].

Spectinomycin is an aminocyclitol antibiotic with broad spectrum antibacterial activity [C. Lewis and H. W. Clapp, "Actinospectacin, A New Antibiotic III. In Vitro and In Vivo Evaluation", *Antibiotics and Chemotherapy*, 2, pp. 127–33 (1961); J. A. Washington and P. K. W. Yu, "In vitro Antibacterial Activity of Spectinomycin", *Antimicrob. Agents Chemother.*, 2, pp. 427–30 (1972)]. Spectinomycin was first prepared by a microbiological process, Bergy et al. U.S. Pat. No. 3,234,092. Spectinomycin is not an aminoglycoside and lacks some of the potential toxicity of that antibiotic group [E. Novak et al., "Animal and Human Tolerance of High-Dose Intramuscular Therapy with Spectinomycin", *J. Infect. Disease*, 130, pp. 50–55 (1974)]. Spectinomycin achieves high serum and urine levels in humans [J. G. Wagner et al., "Absorption, Distribution and Elimination of Spectinomycin Dihydrochloride In Man", *Int. J. Clin, Pharmacol.*, 14, pp. 261–85 (1967)] and has been successfully used to treat a variety of infections [C. E. Cornelius and G. Domescik, "Spectinomycin In the Treatment of Uncomplicated Gonorrhoea", *Br. J. Vener. Dis.*, 46, pp. 212–13 (1970); R. I. Lindemeyer et al., "An Evaluation of a New Antibiotic, Actinospecticin, in Infections of the Urinary Tract", *Am. J. Med. Sci.*, pp. 480–83, (October 1962)]. However, spectinomycin is generally less active in vitro than the amminoglycosides and has been used primarily for treatment of uncomplicated anogenital gonorrhea [*Physicians Desk Reference*, 35th ed., Medical Econimics Co. p. 1844 (1981)].

There are few references to spectinomycin analogs with modified sugar rings in the literature. For example, see U.S. Pat. Nos. 4,351,771, 4,361,701 and 4,173,647.

Modifications at the C-6' position to produce spectinomycin analogs with modified sugar rings are known. Such previously known modifications at the C-6' position can be found in U.S. Pat. Nos. 4,351,771 and 4,361,701 as well as in U.S. application Ser. No. 449,304, filed Dec. 13, 1982, now pending, which is a continuation-in-part of U.S. application Ser. No. 359,723, filed March 1982. Application Ser. No. 449,304 describes, inter alia, the preferred spectinomycin analogs modified at the C-6' position useful in this invention and is incoporated herein by reference.

Modifications at the C-3' position to produce spectinomycin analogs are also known. For example, U.S. Pat. No. 4,465,848 describes, inter alia, the preferred spectinomycin analogs modified at the C-3' position useful in this invention and is also incorporated herein by reference.

The compounds of Ser. No. 449,304 inhibit the growth of microorganisms in various environments. For example, Formula I compounds therein having the $\beta$ configuration are active against *Escherichia coli* and can be used to reduce, arrest, and eradicate slime production in papermill systems caused by its antibacterial action against this microorganism. Still further, $\beta$-anomers are active againsst *Bacillus subtilis* so it can be used to minimize or prevent odor in fish or fish crates caused by this organism. Also, the $\beta$-anomers can be used to swab laboratory benches and equipment in the mycological laboratory. $\beta$-anomers are also effective against *Klebsiella pneumoniae*. The compounds of Formula I therein are also effective for treating bacterial infections, such as gonorrhea in mammals, including humans, D. R. White et al., "Synthesis and In Vitro Antibacterial Properties of Alkylspectinomycin Analogs", *J. of Antibiotics*, 26, pp. 339–42 (1983) discusses, as presently understood, alkylspectinomycin analogs.

The C-3' spectinomycin analogs used in the present invention are known to be active against *E. coli, K. pneumoniae, s. marcescens, S. typhi, s. faecalis, P. vulgaris, P. mirabilis,* and *Ps. aeruginosa*, [see U.S. Pat. No. 4,465,848].

None of the documents cited above make obvious the present invention. Particularly, these documents provide no enablement for the treatment of gonococcal, non-gonococcal, and post-gonococcal urethritis and chlamydia infections by using analogs of spectinomycin.

SUMMARY OF THE INVENTION

The present invention relates to a process for treating gonococcal, non-gonococcal, and post-gonococcal urethritis and chlamydia infections by administering spectinomycin analogs selected from the group consisting of Formula I wherein R is a straight, branched or cyclic alkyl from 1 to 14 carbon atoms and isomeric forms thereof, and Formula II wherein A is $\alpha$-OH:$\beta$-(CH$_2$)$_p$-NR$_{41}$R$_{42}$ or $\alpha$-(CH$_2$)$_p$-NR$_{41}$R$_{42}$:$\beta$-OH, wherein p is 1 or 2, and R$_{41}$ and R$_{42}$, being the same or different, are (i) hydrogen
(ii) alkyl of 1 to 12 carbon atoms, inclusive,
(iii) aryl of 6 to 12 carbon atoms,
(iv) aralkyl of 7 to 12 carbon atoms, inclusive, optionally substituted by one or two
  (1) fluoro, chloro or iodo,
  (2) —$NR_{46}R_{47}$, wherein $R_{46}$ and $R_{47}$ are hydrogen or alkyl of one to 6 carbon atoms, inclusive, being the same or different,
  (3) cyano,
  (4) hydroxy,
  (5) carboxy,
  (6) alkoxycarbonyl of 2 to 5 carbon atoms, inclusive, or
  (7) alkoxy of one to 4 carbon atoms, inclusive,
(v) —$R_{43}$-$R_{44}$, wherein —$R_{43}$— is a single bond or $R_{43}$ is alkylene of 1 to 4 carbon atoms, inclusive, and $R_{44}$ is cycloalkyl of 3 to 10 carbon atoms, inclusive, or
(vi) —CO—$R_{45}$, wherein $R_{45}$ is
(a) alkyl of one to 12 carbon atoms, inclusive, or aryl or aralkyl of 7 to 12 carbon atoms optionally substituted by one or two
  (1) fluoro, chloro or iodo,
  (2) —$NR_{46}R_{47}$, wherein $R_{46}$ and $R_{47}$ are hydrogen or alkyl of one to 6 carbon atoms, inclusive, being the same or different,
  (3) cyano,
  (4) hydroxy,
  (5) carboxy
  (6) alkoxycarbonyl of 2 to 5 carbon atoms, inclusive, or
  (7) alkoxy of one to 4 carbon atoms, inclusive,
(b) —$R_{43}$-$R_{44}$ wherein $R_{43}$ and $R_{44}$ are as defined above, or
(c) pyridyl, piperazyl, pyrollyl or morpholinyl optionally substituted by
  (1) fluoro, chloro or iodo,
  (2) —$NR_{46}R_{47}$, wherein $R_{46}$ and $R_{47}$ are hydrogen or alkyl of one to 6 carbon atoms, inclusive, being the same or different,
  (3) cyano,
  (4) hydroxy,
  (5) carboxy,
  (6) alkoxycarbonyl of 2 to 5 carbon atoms, inclusive, or
  (7) alkoxy of one to 4 carbon atoms, inclusive,
and pharmaceutically acceptable salts and hydrates thereof to birds and mammals including humans in unit dosage forms, such as sterile parenteral solutions or suspensions, eyedrops and water-in-oil emulsions containing suitable quantities of the spectinomycin analogs. Especially effective are compounds of Formula I wherein R is selected from the group consisting of n-propyl, n-butyl, n-pentyl and an alkyl group cyclic or branch chain system, in which the longest extension of the branch or cyclic system contains from 1 to 5 carbon atoms, inclusive. By the processes of the invention it is now possible to treat, for example, *Chlamydia trachomatis* infections of the human genital tract.

DETAILED DESCRIPTION OF THE INVENTION

As used herein, "urethritis" includes gonococcal, non-gonococcal, and post-gonococcal urethritis comprising chlamydial infection.

The processes of the present invention involve presentation of spectinomycin analogs for administration to birds, mammals and humans in unit dosage forms, such as sterile parenteral solutions or suspensions, eye drops and water-in-oil emulsions containing suitable quantities of the spectinomycin analog for treatment of gonococcal, non-gonococcal and post-gonococcal urethritis as well as chlamydia infections including *Chlamydia trachomatis*.

For parenteral administration, fluid unit dosage forms are prepared utilizing the spectinomycin analog and a sterile vehicle, water being preferred. The analog, depending on the vehicle and concentration used, can be either suspended or dissolved in the vehicle. In preparing solutions, the spectinomycin analog can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspension can be prepared in substantially the same manner, the compound is dissolved and sterilization may be accomplished by filtration.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular effect to be achieved and (b) the limitations inherent in the art of compounding such an active material for use in humans, birds and animals. Examples of suitable unit dosage forms in accord with this invention are ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include, for example, the route of administration and the potency of the particular compound, and also the size, weight and species of animal to be treated. A dosage schedule for humans of from about 0.2 to about 4000 mg of compound in a single dose, administered parenterally or in the compositions of this invention, are effective for bacterial infections. More specifically, the single dose is from 0.5 mg to about 200 mg of compound.

The following examples describe the processes and methods of this invention and are indicative of the scope of this invention but are not to be construed as limitative. Those skilled in the art will recognize variations from the procedures in the analogs used, in the novel methods described.

Assay I for Determining Antimicrobial Activity Against *Chlamydia Trachomatis*

1. Chlamydial Growth System

McCoy cells are grown on 13 mm cover slips in glass vials for three passages in the absence of antibiotics. Confluent monolayers are treated with 10 µg/ml 5-iodo-2-deoxyuridine (IUDR) in overlay medium for 72 hrs. The IUDR is removed and the vials are inoculated with 0.2 ml of chlamydial stock strain G-29 (E/UW-17/cx) diluted to yield about $3.0 \times 10^3$ inclusions per cover slip. The inoculated vials are centrifuged for 60 min at 2-3000×g, and overlaid with 1 ml maintenance medium, with or without the spectinomycin analog under test. No other antibiotic is included in this medium.

Vials are incubated for 72 hrs at 35° C.; iodine stained, and the inclusions in 20 high-power fields are counted and averaged.

2. Toxicity Testing

The above described chlamydial growth system is employed, using three vials per concentration of drug. No antibiotics are used in any medium employed and no vials are inoculated with chlamydia. The spectinomycin analog is tested at two concentrations for toxicity.

The C-1 concentration is the upper limit concentration level and the C-1 concentration is one 10-fold dilution of the C-1 concentration. Vials are observed after 72 hr incubation at 35° C. with medium containing C-1 or C-10 concentrations of the analog in maintenance medium.

If no toxicity is observed, work proceeds to 3. If both C-1 and C-10 concentrations show toxicity, results are recorded. If C-1 shows toxicity but C-10 does not, the toxic level is determined, using 2-fold dilutions of C-1 through C-10. Work then proceeds to 3., using the highest nontoxic level of the analog.

3. Inhibitory Efficacy Testing

Three vials of McCoy cells grown as described in 1. are used for each drug concentration and for each control. Drug concentrations consist of C-1 and C-10, unless either has been found to be toxic. If so, the highest nontoxic drug concentration, as found in 2. is used and its 10-fold dilution. Tests consist of three vials each for C-1 and C-10 with inoculum as efficacy testing; and three vials each for C-1 and C-10 without inoculum for toxicity testing. Three vials are used for a negative control, consisting of overlay medium without any drug. Three vials are used for a positive control, consisting of either erythromycin or tetracycline at 99% MIC in the overlay medium, with and without inoculum.

The growth system is as described in 1. Average counts of inclusions are determined for the three cover slips of each system. Counts for C-1 and C-10 are compared to counts for the negative control to determine whether either drug concentration shows ≧99% inhibition, when the control drug shows that effect without toxicity in any test or control system. If neither drug concentration produces ≧99% inhibition results are recorded.

4. If ≧99% reduction in inclusions is seen, the 90% and 99% MIC is determined, using appropriate 2-fold dilutions of drug and the same experimental design as described in 3.

Assay II for Determining Antimicrobial Activity Against *Chlamydia trachomatis*

Standard inoculum of the chlamydial isolate, pretitrated to yield approximately 100-300 inclusions per coverslip, is used to infect cycloheximide-treated McCoy cells. The inoculum is centrifuged into the cells (−2500 g for 1 hour) and allowed to incubate at 37C for 2 hrs. The tissue culture medium is then replaced with medium containing the appropriate spectinomycin analog. Each dilution is tested in triplicate and one tube is used for passage into three new cell monolayers. After centrifugation of passage material, the monolayers are washed several times with medium containing no spectinomycin analog and then incubated for 3 days at 37C. Coverslips are stained with Giemsa stain and microscopically examined at 250x. The entire coverslip is examined and the number of iodine-staining inclusions per coverslip counted. The initial passage in antibiotic-supplemented medium (designated "I" in Table 1) determines the inhibitory concentration of each analog. The passage into cell monolayers with drug-free medium (designated "II" in Table 1) determines the chlamydicidal concentration of each analog. Inoculum and toxicity control tubes are included in each experiment.

EXAMPLE I

U-63,366F (6′-propyl spectinomycin·$H_2SO_4$·$5H_2O$), U-63,538E (6′-pentyl spectinomycin·2HCl), U-65,551E ((3′-R)-3′-[(pentylamino)methyl]3′-dihydrospectinomycin·3HCl), and spectinomycin were assayed for anti-chlamydial activity according to the procedure set forth in Assay I with the following results:

| | MIC for ≧90% Reduction (μg/ml) | MIC for ≧99% Reduction (μg/ml) |
|---|---|---|
| U-63,366F | 1.56 | 3.51 |
| U-63,538E | 0.49 | 1.95 |
| U-65,551E | 125 | 125 |
| Spectino-mycin | 62.5 | 250 |

The MIC values for spectinomycin agree with the literature indicating that spectinomycin has marginal activity against *C. trachomatis.* 6′-propyl spectinomycin (U-63,366F) was about 40–70 times more active than spectinomycin, depending upon which endpoint is compared. 6′-pentyl spectinomycin was about 128 times more active than spectinomycin and about twice as active as 6′-propyl spectinomycin. (3′-R)-3′-[pentylaminomethyl]-3′-dihydrospectinomycin (U-65,551E) had activity comparable to spectinomycin.

EXAMPLE II

U-60,734E (6′-methyl spectinomycin), U-63,466E (6′-n-octyl spectinomycin), and U-62,939E (3′-aminomethyl dihydrospectinomycin) were assayed for anti-chlamydial activity according to the procedure set forth in Assay II with the results set forth in Table 1:

TABLE 1

| Drug Concentration (μg/ml) | Number of Inclusions per Coverslip* and Percentage of Original Inoculum Remaining for Spectinomycin and Analogs: Spectinomycin U-18409E | | | Analog U-60734E | | | Analog U-63466E | | | Analog U-62939E | | |
|---|---|---|---|---|---|---|---|---|---|---|---|---|
| | I[a] | II[b] | Toxic[c] | I | II | Toxic | I | II | Toxic | I | II | Toxic |
| 100 | 18 9% | —[e] | No | — | 2 | No | | | Yes | — | — | Yes |

TABLE 1-continued

Number of Inclusions per Coverslip* and Percentage of Original Inoculum Remaining for Spectinomycin and Analogs

| Drug Concentration (μg/ml) | Spectinomycin U-18409E | | | Analog U-60734E | | | Analog U-63466E | | | Analog U-62939E | | |
|---|---|---|---|---|---|---|---|---|---|---|---|---|
| | I[a] | II[b] | Toxic[c] | I | II | Toxic | I | II | Toxic | I | II | Toxic |
| 10 | 65 31% | +[d] | No | 89 51% | + | No | | | Yes | 11 14% | + | No |
| 1 | —[e] | + | No | 130 75% | + | No | | | Yes | 16 20% | + | No |
| Inoculum Control | 209 | | | 173 | | | 81 | | | 81 | | |

*Average of three coverslips
I[a] — First passage; determines inhibitory activity
II[b] — Second passage; determines chlamydicidal activity
Toxic[c] — Toxicity for McCoy cells
+[d] — Too many inclusions to count, or more than control
—[e] — No inclusions (0% remaining)

Spectinomyciin demonstrated relatively poor anti-C. trachomatis activity. The compound was slightly inhibitory at 10 and 100 μg/ml and was cidal within the same range. 6'-methyl spectinomycin (U-60,734E) was more inhibitory than spectinomycin, but was not totally cidal even at 100 μg/ml. 3'-aminoethyl dihydrospectinomycin (U-62,939E) was the most active spectinomycin analog, inhibiting 80% of inclusion formation at 1 μg/ml, however, the drug concentration required for cidal activity was between 10 and 100 μg/ml. 6'-n-octyl spectinomycin (U-63,466E) was very toxic to the McCoy cells at every drug concentration tested and an assessment of antichlamydial activity could not be made.

EXAMPLE III

This example demonstrates the activity of an antichlamydial spectinomycin analog against several strains of C. trachomatis.

Antibiotic U-63,366F (6'-propyl spectinomycin) was assayed at various times according to Assay I with several strains substituted for strain G-29. The results are set forth in Table 2.

TABLE 2
The Activity of U-63,366F and Spectinomycin Against Chlamydia trachomatis

| Sources Strain | Antibiotic | 90%[a] MIC (μg/ml) | 99%[b] MIC (μg/ml) |
|---|---|---|---|
| G-29 | U-63,366 | 1.56 | 3.51 |
| G-29 | Spectinomycin | 62.5 | 250 |
| Tric-91 | U-63,366F | 6.25 | 12.5 |
| P-1 | U-63,366F | 6.25–12.5 | 6.25–12.5 |
| P-6 | U-63,366F | −6.25 | 12.5 |
| P-7 | U-63,366F | −6.25 | 12.5 |
| Ur/B-5 | U-63,366F | 6.25 | 12.5 |
| E/UW-17/Cx [G-29] | U-63,366F | 6.25 | 12.5 |
| E/UW/680/Cx | U-63,366F | 6.25 | 12.5 |
| Mayo Cx/P-2 | U-63,366F | 6.25 | 12.5 |

[a]Concentration required to inhibit 90% of inclusion formation
[b]Concentration required to inhibit 99% of inclusion formation As can be seen from Table 2, U-63,366F demonstrated a significant level of activity as compared to spectinomycin against eight strains of Chlamydia trachomatis, with 99% MIC values from 3.51 to 12.5 μg/ml.

While we have presented a number of embodiments of this invention, it is apparent that the basic methods can be altered to provide other embodiments which utilize the methods and compositions of this invention. Therefore, it will be appreciated that the scope of this invention is to be defined by the claims appended hereto rather than the specific embodiments which have been presented above by way of example.

FORMULAS

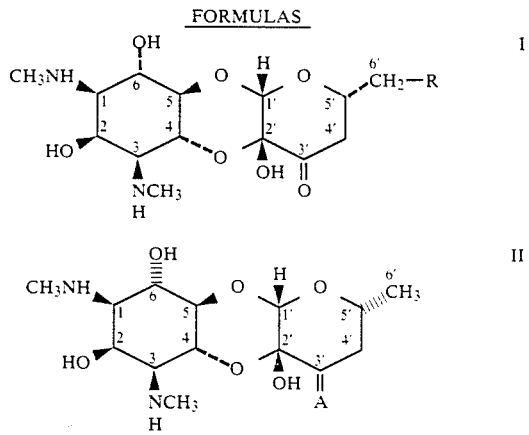

We claim:

1. A method of treating chlamydial infection comprising administering an anti-chlamydial effective amount of spectinomycin analog selected from the group consisting of

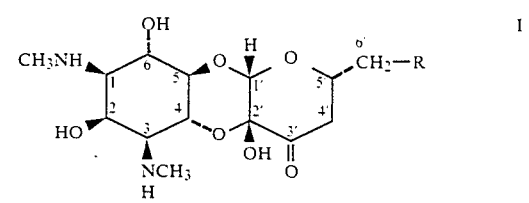

wherein R is a straight, branched or cyclic alkyl from 1 to 4 carbon atoms and isomeric forms thereof, and pharmaceutically acceptable salts and hydrates thereof to a host in need of said treatment.

2. The method of claim 1 wherein R is selected from the group consisting of n-propyl, n-butyl, n-pentyl and an alkyl group cyclic or branch chain system, in which the longest extension of the branch or cyclic system contains from 1 to 5 carbon atoms, inclusive.

3. The method of claim 1, wherein the host is selected from the group consisting of birds, mammals, and humans.

4. The method of claim 1 wherein the spectinomycin analog is selected from the group consisting of 6'-ethylspectinomycin, 6'-ethylspectinomycin dihydrochloride,
6'-n-propylspectinomycin,
6'-n-propylspectinomycin dihydrochloride
6'-n-propylspectinomycin sulphate,
6'-n-butylspectinomycin,
6'-n-butylspectinomycin dihydrochloride,
6'-iso-butylspectinomycin,
6'-iso-butylspectinomycin dihydrochloride,
6'-n-pentylspectinomycin,
6'-n-pentylspectinomycin dihydrochloride
6'-(3,3-dimethyl)-n-butylspectinomycin,
6'-(3,3-dimethyl)-n-butylspectinomycin dihydrochloride,
6'-cyclopentylmethylspectinomycin,
6'-cyclopentylmethylspectinomycin dihydrochloride,
6'-cyclohexylmethylspectinomycin and
6'-cyclohexylmethylspectinomycin dihydrochloride.

5. The method of claim 1 wherein the spectinomycin analog is selected from the group consisting of 6'-n-propylspectinomycin, 6'-n-propylspectinomycin dihydrochloride and 6'-n-propylspectinomycin sulphate.

6. The method of claim 1 wherein the spectinomycin analog is selected from the group consisting of 6'-n-pentylspectinomycin and 6'-n-pentylspectinomycin dihydrochloride.

7. A method of treating chlamydia related urethritis comprising administering an antiurethritis effective amount of spectinomycin analog selected from the group consisting of

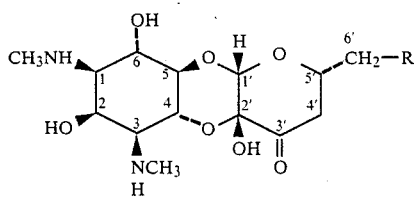

wherein R is a straight, branched or cyclic alkyl from 1 to 14 carbon atoms and isomeric forms thereof, and pharmaceutically acceptable salts and hydrates thereof to a host in need of said treatment.

8. The method of claim 7 wherein R is selected from the group consisting of n-propyl, n-butyl, n-pentyl and an alkyl group cyclic or branch chain system, in which the longest extension of the branch or cyclic system contains from 1 to 5 carbon atoms, inclusive.

9. The method of claim 7 wherein the host is human.

10. The method of claim 7 wherein the spectinomycin analog is selected from the group consisting of
6'-ethylspectinomycin,
6'-ethylspectinomycin dihydrochloride,
6'-n-propylspectinomycin,
6'-n-propylspectinomycin dihydrochloride
6'-n-propylspectinomycin sulphate,
6'-n-butylspectinomycin,
6'-n-butylspectinomycin dihydrochloride,
6'-iso-butylspectinomycin,
6'-iso-butylspectinomycin dihydrochloride,
6'-n-pentylspectinomycin,
6'-n-pentylspectinomycin dihydrochloride
6'-(3,3-dimethyl)-n-butylspectinomycin,
6'-(3,3-dimethyl)-n-butylspectinomycin dihydrochloride,
6'-cyclopentylmethylspectinomycin,
6'-cyclopentylmethylspectinomycin dihydrochloride,
6'-cyclohexylmethylspectinomycin and
6'-cyclohexylmethylspectinomycin dihydrochloride.

11. The method of claim 7 wherein the spectinomycin analog is selected from the group consisting of 6'-n-propylspectinomycin, 6'-n-propylspectinomycin dihydrochloride and 6'-n-propylspectinomycin sulphate.

12. The method of claim 7 wherein the spectinomycin analog is selected from the group consisting of 6'-n-pentylspectinomycin and 6'-n-pentylspectinomycin dihydrochloride.

* * * * *

UNITED STATES PATENT AND TRADEMARK OFFICE
CERTIFICATE OF CORRECTION

PATENT NO. : 4,895,870

DATED : January 23, 1990

INVENTOR(S) : Gary E. Zurenko, James J. Vavra, David R. White, Richard C. Thomas It is certified that error appears in the above-identified patent and that said Letters Patent is hereby corrected as shown below:

Column 8, lines 54-55, "from 1 to 4 carbon atoms" should read --from 1 to 14 carbon atoms--.

Signed and Sealed this

Twenty-third Day of July, 1991

*Attest:*

HARRY F. MANBECK, JR.

*Attesting Officer*   Commissioner of Patents and Trademarks